United States Patent [19]

Reuther

[11] Patent Number: 5,059,531

[45] Date of Patent: Oct. 22, 1991

[54] PROCESS FOR THE PREPARATION OF PILOCARPINE FROM IN VITRO CULTURES OF PILOCARPUS

[75] Inventor: Gerhard R. Reuther, Geisenheim, Fed. Rep. of Germany

[73] Assignee: Merck Patent Gesellschaft Mit Beschränkter Haftung, Darmstadt, Fed. Rep. of Germany

[21] Appl. No.: 673,559

[22] Filed: Mar. 22, 1991

[30] Foreign Application Priority Data

Mar. 23, 1990 [DE] Fed. Rep. of Germany ....... 4009392

[51] Int. Cl.$^5$ .................... H01H 4/00; C07D 405/06; C12P 17/16
[52] U.S. Cl. .................................. 435/118; 435/119; 435/240.48; 435/240.5; 514/397; 548/346
[58] Field of Search ..................... 435/118, 119, 240.5, 435/240.48; 514/397; 548/346

[56] References Cited

U.S. PATENT DOCUMENTS

| | | | |
|---|---|---|---|
| D. 497,015 | 11/1990 | Yamamoto et al. | 435/119 |
| 3,761,595 | 9/1973 | Pfeffer | 514/397 |
| 4,673,648 | 6/1987 | Wilcox et al. | 435/240.5 |
| 4,684,612 | 6/1987 | Hemphill et al. | 435/240.5 |

*Primary Examiner*—Herbert J. Lilling
*Attorney, Agent, or Firm*—Millen, White & Zelano

[57] ABSTRACT

Pilocarpine is isolated from Pilocarpus from suspension cultures of from in vitro cultures of differentiated plants, where, to establish the in vitro cultures, specific culture media are used which differ in their hormone composition and which are used in a particular sequence.

12 Claims, No Drawings

PROCESS FOR THE PREPARATION OF PILOCARPINE FROM IN VITRO CULTURES OF PILOCARPUS

BACKGROUND OF THE INVENTION

The invention relates to a process for the preparation of pilocarpine from suspension cultures or differentiated in vitro plant cultures of the genus Pilocarpus. The woody plant of the genus Pilocarpus with its most important representatives *P. jaborandi* and *P. microphyllus*, which is indigenous to South America, contains, inter alia, the imidazole alkaloid pilocarpine.

Pilocarpine is used as a pharmaceutical or therapeutic substance. It is a parasympathomimetic which acts directly. It has a muscarine- and acetylcholine-type action with the advantage that it cannot be degraded by choline esterase. It enhances the secretion of the perspiratory glands and salivary glands and stimulates the smooth muscles of the bowels and of the bronchial tubes. Nowadays, ophthalmology is virtually the only field of application. Since, as a myotic, it reduces the intraoccular pressure, it is preferably employed for treating glaucoma.

Obtaining pilocarpine via a chemical or biochemical route has proved to be difficult and, so far, uneconomical. The demand for pilocarpine is therefore substantially covered from the plant itself by isolation and purification of the alkaloid. However, the seeds of Pilocarpus retain the ability to germinate only for a very brief time, as is also the case in many other tropical plants. The germination percentage drops by more than 90% within a few weeks. This means that Pilocarpus seedlings can only be successfully grown near the sites in which they grow naturally. Another disadvantage is the slow growth of seedlings under greenhouse conditions.

On the other hand, attempts to culture Pilocarpus in vitro have failed so far. In general, the success of an in vitro culture of woody plants, in particular from callus, can only be ensured in exceptional cases, and this is only the case with relatively undemanding species which do not present problems (Bonga and Durzan (1987), Cell and Tissue Culture in Forestry, Vol. 1-3, Martinus Nijhoff Publishers; Chalupa (1987) in: Bonga and Durzan (1987), l.c.; Wann (1988), Horticultural Reviews 10, 153). Besides the fact that in vitro culture as such is difficult, it is also extremely doubtful if the resulting in vitro cultures are still capable of synthesizing acceptable amounts of the desired natural product, in this case pilocarpine. A large number of such cultures have proved to be useless for practical purposes.

It was therefore the object to develop a process for the preparation of pilocarpine from plant material on the basis of an in vitro culture capable of alkaloid formation, so that the above-mentioned disadvantages as regards site and growth conditions can be avoided.

SUMMARY OF THE INVENTION

It has now been found that an in vitro tissue culture which is capable of propagation and the formation of pilocarpine can be prepared from explants of organ fragments of seeds and, in particular, young seedlings of Pilocarpus. It is possible to obtain suspension cultures and also differentiated cultures. For these purposes, a very particular composition and sequence of hormones, or hormone-containing nutrient media, are preferred when preparing the above-mentioned cultures.

The invention therefore provides a process for preparing pilocarpine by isolation and purification from Pilocarpus, characterized in that cultures grown in vitro are employed.

In particular, the invention relates to an appropriate process, which is characterized in that, to obtain the in vitro culture, a callus which is derived from organ explants is produced on a suitable nutrient medium, shoot differentiation of the callus is induced on a series of various nutrient media, each of which contains specific hormones, and by culturing the cells thus obtained in a liquid nutrient solution or, after root formation has been induced, as a differentiated plant.

Upon further study of the specification and appended claims, further objects and advantages of this invention will become apparent to those skilled in the art.

The process according to the invention is preferably carried out as follows.

Any species of Pilocarpus can be used as a source of tissue for culturing according to this invention.

Preferably suitable for culturing Pilocarpus are the species *Pilocarpus jaborandi* and *Pilocarpus microphyllus* but, in particular, *P. microphyllus*. A callus culture is first prepared in a manner known per se. For this purpose, it is possible to use either seeds or organ explants from Pilocarpus seedlings.

However, callus formation from seedlings is preferred, since calli obtained from seeds are generally not capable of a sufficient degree of shoot formation. However, the propagation of shoots is preferred for the process according to the invention. To obtain callus from seedling explants, it is preferred to use seedlings of from 8 to 12 cm in length as the starting material. Suitable examples of primary explants are shoot-tip explants or leaf-stalk segments. However, it is particularly preferred to use shoot-tip explants for callus formation because of their higher regeneration activity. The explants, or seedlings, are prepared or sterilized in a manner known per se, placed on a solid nutrient medium at temperatures between about 22° C. and 27° C., preferably 25° C., with illumination, and cultured for several weeks following standard procedures. These culture conditions are also preferred for the entire process according to the invention. The basic nutrient media which can be used are those which are particularly suitable for woody plants, for example the Woody Plant Medium (WPM) (Lloyd and McCown (1980), Proc. Inter. Plant Prop. Soc. 30. 421) or variants thereof. The qualitative and quantitative composition of this basal medium (without hormones) can be varied within a certain range without having substantial effects on the process according to the invention. The amount of sugar, in particular, can be varied within a substantial range (e.g., 10–40 g/l, preferably 20 g/l). The basal medium is suitable for both liquid media and solid nutrient media (addition of gelling agents, for example agar or Gelrite ® (Merck & Co., Inc., USA)). A detailed composition is given in the exemplary embodiments. A key feature of the invention is, inter alia, the qualitative and quantitative composition of the hormone components which must be added to the basal medium so that optimum vegetative propagation of the Pilocarpus explants can take place.

The formation of, in particular organogenic, callus tissue from the Pilocarpus explants is effected according to the invention by adding the three hormones α-naphthylacetic acid, N⁶-dimethylallyladenine and zeatine to the WPM basal medium. The concentration in the case of naphthylacetic acid is 0.75 to 1.25 mg/l, preferably 1.0 mg/l, in the case of dimethyladenine 0.3 to 0.7 mg/l, preferably 0.5 mg/l, and in the case of zeatine likewise 0.3 to 0.7 mg/l, preferably 0.5 mg/l. Culture on the hormone-containing medium (M3 medium) causes callus formation always showing organ structures with many types of differentiation. It is surprising that differentiated somatic embryos, inter alia, can be induced by adding the appropriate hormones. This has not been observed to date in callus vegetative plant material from woody plants, or not to the same degree. From the organogenic callus tissue, it is preferred to establish several subcultures on the M3 medium in a manner known per se. Together with the illumination, the medium enhances the formation of a large number of organs. On this medium, the callus has a high induced embryogenic potency. However, it is not possible to achieve sufficient shoot development with the aid of the M3 medium. The growth of shoots, however, is highly important for the further development of a functional in vitro culture.

Surprisingly, shoot formation can now be caused by transferring the organogenic callus tissue to a nutrient medium with a different hormone composition. An example of a suitable basal medium, again, is the WPM medium in the same or in a varied composition, or comparable other media. Instead of the hormone composition of the M3 medium, the subsequent medium contains, according to the process according to the invention, only 6-benzylaminopurine in a concentration between about 0.3 and 0.8 mg/l, but preferably between 0.4 and 0.6 mg/l. This hormone-containing medium (betula medium) induces and/or markedly enhances shoot growth, in some cases up to tufts of shoots, and shoot elongation. In this procedure, the effect is generally more apparent in the second and subsequent subculture. The duration of one subculture is generally about 30 to 60 days, preferably 40 days, depending on the plant material and external conditions, such as temperature, illumination, etc. The advantageous effect of the hormone addition according to the invention can be illustrated in particular by the fact that, when the cultures which have been grown on betula medium in the second step are retransferred, shoot growth is reduced very rapidly to one-fifth to one-tenth.

After several subcultures, the culture which has undergone differentiation in this way may be placed on a fresh medium, preferably WPM medium, which contains the hormones 6-benzylaminopurine and indole-3-acetic acid (DKW medium). 6-Benzylaminopurine is used here in a concentration of about 0.3 to 0.8 mg/l, preferably 0.4 to 0.6 mg/l, and indole-3-acetic acid in a concentration from about 0.05 to 0.2 mg/l, preferably from 0.08 to 0.15 mg/l. The DKW medium further enhances shoot propagation and moreover conditions the shoots for root formation which takes place later. Such root formation is necessary for obtaining a differentiated plant culture in a further process step. To prepare a pure suspension culture, for which root formation of the tufts of shoots is of no importance, it is also possible to dispense with the transfer of the culture from the betula to the DKW medium, without this resulting in decisive disadvantages. Vice versa, the betula medium can also be dispensed with, if necessary, if a differentiated plant culture is prepared. In any case, it is essential for the process according to the invention that the sequence of medium and hormones M3/betula or M3/DKW, but preferably in all cases the media sequence M3/betula/DKW, is adhered to. The use of the M3 medium as the primary medium is essential in any case, since culturing the explants exclusively on betula or DKW results in the formation of an insufficient amount of callus, or that the amount of callus is consumed. To prepare suspension cultures, the corresponding betula or DKW media are used without gelling agents.

The known methods for root formation in shoot cultures, by enriching the media with auxins, are not successful in the case of Pilocarpus. However, it is surprising that root formation can be induced by the following process steps. Under sterile conditions, the shoots are immersed in an aqueous auxin solution up to a depth of not more than 3 mm. The auxin concentration employed must be extremely high, from 0.8 to 1.5 g/l, preferably 1.0 to 1.2 g/l. Examples of suitable auxins are indole acetic acid, indole butyric acid or α-naphthyl acetic acid. However, indole butyric acid is particularly preferred. Immersion is effected over a period of three to six minutes, preferably 5 minutes. The shoot culture which has been treated in this way is preferably precultured on the DKW medium and subsequently transferred to a hormone-free medium, for example WPM together with a gelling agent. Gelrite ® is preferred to agar since it increases root formation of the Pilocarpus culture by a factor of approximately 3 to 5. Furthermore, root induction enhances shoot growth. The resulting differentiated Pilocarpus in vitro cultures can be cultured on a suitable nutrient medium, preferably DKW, several subculture steps being carried out. However, they can also be transplanted into soil after a few subculture steps have been carried out, and grown in a manner known per se under suitable greenhouse conditions.

Pilocarpine can be obtained according to the invention from both suspension cultures and differentiated cultures. The alkaloid is isolated and purified by standard methods, e.g., according to Petit et al. (1897), Bull. Soc. Chim. 17, 537.702, and/or Ullmanns Enzyclopädie der technischen Chemie 3, 277 (1953), and explained in greater detail in the exemplary embodiments. The purified alkaloid content in the differentiated cultures is about 0.01 to 0.2% (w/w) based on the total weight of the plant material employed, usually about 0.05 to 0.1%. This corresponds to about one-fifth to one-twentieth of the amount of alkaloid in naturally grown Pilocarpus at the indigenous site. In the case of suspension cultures, the alkaloid content is yet again lower than in the differentiated in vitro cultures by a factor of ten, that is to say between about 0.001% and 0.05%, in particular between 0.005% to 0.02% (w/w). This means that an average of 100 mg of pilocarpine can be isolated from approximately 1 kg of suspension culture.

The pilocarpine isolated according to the present invention is used analogously to pilocarpine isolated by standard methods, e.g., for the treatment of glaucoma, in the usual amounts, e.g., 0.1 to 1.5 mg/eye, applied as a 0.5–4% solution 1 to 5 times a day.

Using the process according to the invention, *Pilocarpus microphyllus* gives suitable in vitro cultures with correspondingly higher alkaloid yields more rapidly and more easily than *P. jaborandi*.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 09 392.1, are hereby incorporated by reference.

EXAMPLES

Example 1

Preparation of a callus culture from seeds

Seeds of *P. microphyllus* are sterilized for 2 hours in an aqueous sodium hypochlorite solution (5%). They are then washed 3 times for 10, 20 and 30 minutes using a sterile 1:1 mixture of tap water and demineralized water. The seed coat is peeled off, and the peeled seeds are halved lengthwise, and the halves are placed with the cut surface on an M3 medium (composition in Example 2), and the seeds are halved widthwise. They are incubated in an incubation cabinet at 25°-27° C. in the dark. After 7 weeks, callus pieces which have been formed are excised from primary explants (cut edges) and placed on fresh M3 medium. The cultures are grown at about 25° C. and illuminated in a 16-hour-day (3–4 klux mixed light from a daylight source and a warm-tone source), until, after several subculture steps have been carried out (4–5 weeks/step), there exists a green callus culture which can undergo shoot organogenesis.

Example 2

Preparation of a callus culture from seedling explants

*Pilocarpus microphyllus* seeds are germinated in a TKS/sand mixture under warm greenhouse conditions. When the seedlings have reached a height of about 10 cm, they are cut off about 1 cm above the soil. For decontamination, the material is immersed for 20 seconds in 70% ethanol and then for 12 minutes in 5% NaOCl solution with the addition of 1 drop of Tween 20. This is followed by 3 washes with sterile water, twice for 10 minutes and once for 30 minutes. Shoot tips or shoot segments, 1 to 3 mm in size, are excised from the plant material and placed on the M3 medium indicated below. The culture are maintained in the light in a 16-hour-day (3–4 klux mixed light from a daylight source and a warm-tone source) at 25° C. Greenish callus lumps form after 10–12 weeks and are subcultured several times. All procedures are carried out under sterile conditions. One subculture step takes 4–5 weeks. The amount of callus increased constantly. In some cases, the callus has pronounced organ features, so, for example, differential somatic embryos. However, shoot growth is virtually non-existent.

| Macroelements: | mg/l | Microelements: | mg/l |
|---|---|---|---|
| WPM medium (hormone-free): | | | |
| $K_2SO_4$ | 990 | $H_3BO_3$ | 6.2 |
| $NH_4NO_3$ | 400 | $MnSO_4.H_2O$ | 16.9 |
| $CaCl_2.2 H_2O$ | 96 | or | |
| $Ca(NO_3)_2.4 H_2O$ | 556 | $MnSO_4.4 H_2O$ | 22.3 |
| $MgSO_4.7 H_2O$ | 370 | $NaMoO_4.2 H_2O$ | 0.25 |
| $KH_2PO_4$ | 170 | $CuSO_4.5 H_2O$ | 0.25 |
| $FeSO_4.7 H_2O$ | 27.8 | | |
| $Na_2EDTA$ | 37.3 | | |
| Organic Components: | | | |
| Glycine | 2.0 | | |
| Nicotinic acid | 0.5 | | |
| Pyridoxine HCl | 0.5 | | |
| Thiamine HCl | 1.0 | | |
| Meso-inositol | 100 | | |
| Sucrose | 20 g/l | | |
| Difco agar | 7 g/l | (not in the case of suspension cultures) | |
| M3-medium: | | | |
| WPM medium (hormone-free) | | | |
| α-Naphthyl acetic acid | 1.0 mg/l | | |
| $N^6$-Dimethylallyladenine | 0.5 mg/l | | |
| Zeatine | 0.5 mg/l | | |

Example 3

Preparation of a suspension culture a) The organogenic callus culture established in accordance with Example 1 or 2 is placed under sterile conditions on a liquid betula medium (without agar or Gelrite®) and cultured in several subculture steps (about 2–4 weeks/step) under the conditions indicated in Examples 1 and 2 and with constant slight shaking. This results in an intensive shoot development and shoot multiplication.

Betula medium
  WPM medium (hormone free, analogous to Example 2, without agar)
  6-Benzylaminopurine 0.5 mg/l b) The suspension culture obtained in accordance with Example 3a is placed in a liquid DKW medium and cultured in several subculture steps.

DKW medium
  WPM medium (hormone-free, analogous to Example 2, without agar + additionally 10 g/l sucrose).
  6-Benzylaminopurine 0.5 mg/l
  Indole-3-acetic acid 0.1 mg/l

EXAMPLE 4

Establishing rooted plant culture a) The callus culture established in accordance with Example 1 or 2 is placed under sterile conditions on a betula medium (analogous to Example 3a+agar) and several subculture steps (about 4–5 cultured in several subculture steps (about 4–5 weeks/step) under the conditions indicated in Examples 1 and 2. This results in an intensive shoot development and shoot multiplication, with a tendency to tuft formation.

b) The shoot cultures established in accordance with a) are placed on a DKW medium (analogous to Example 3b+ agar) and subcultured several times as under a). The cultures are now conditioned for root formation.

c) The shoot cultures established in accordance with Example 3b or 4b are treated as follows:
  the extreme tip (about 2–3 mm) of the shoots is immersed for 5 minutes into an aqueous solution of indole butyric acid (1000 mg/l),
  a shoot preculture is grown analogously to Example 4b,
  the culture is transferred to hormone-free WPM medium with 3 g/l Gelrite® when the shoots have reached a size of 15 to 20 mm, if desired, the material is transplanted into soil and gradually acclimatized to non-sterile conditions.

Example 5

Isolation and purification of pilocarpine 320 g of the plant material obtained in accordance with Example 4 are dried at 30° C. and subsequently ground finely. The material is taken up in 400 ml of chloroform and 25 ml of 10% ammonia solution, and the mixture is stirred for 20 minutes. The mixture is then filtered through a cotton wool ball into a separation funnel which contains 250 ml of 5% sulfuric acid and shaken for about 1 minute. When phase separation has occurred, the chloroform phase is discarded. The aqueous residue which contains the drug is re-extracted using 250 ml of fresh chloroform, the extract is filtered over a cotton wool ball, and the filtrate is extracted by shaking with 250 ml of 5% sulfuric acid. The aqueous solution is carefully evaporated on a rotary evaporator to about half the volume. Pilocarpine hydrochloride starts to crystallize in the cold. Yield 285 mg.

The analytical detection is effected via HPLC:
Column: LiChrocart 125-4-RP-Select B ®, with Li-Chrospher 60 ®, 5 μm (E. Merck, Darmstadt, FRG)
Eluant: 5% aqueous $KH_2PO_4$ solution, pH 2.5
Column temperature: 45° C.
Flow rate: 2 ml/minute
Detection: 216 nm The preceding examples can be repeated with similar success by substituting the generically or specifically described reactants and/or operating conditions o this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of pilocarpine, comprising isolating the pilocarpine from a culture of Pilocarpus cells grown in vitro wherein the in vitro culture is obtained by producing a callus, derived from an organ explant of Pilocarpus, on a nutrient medium, inducing shoot differentiation of the callus on a series of nutrient media containing hormones, and culturing the thus-obtained cells in a liquid nutrient medium, or inducing root formation and culturing the thus-obtained differentiated plant.

2. A process of claim the in vitro culture is a suspension culture.

3. A process of claim 1, wherein the in vitro culture is a differentiated plant culture.

4. A process of claim 1, wherein the shoot differentiation is induced by a series of nutrient media containing, in the order indicated, the hormones
   a) α-naphthyl acetic acid, $N^6$-dimethylallyladenine and zeatine,
   b) 6-benzylaminopurine and/or
   c) 6-benzylaminopurine and indole-3-acetic acid.

5. A process of claim 1, wherein the shoot differentiation is induced by a series of nutrient media containing, in the order indicated, the hormones
   a) α-naphthyl acetic acid, $N^6$-dimethylallyladenine and zeatine and
   b) 6-benzylaminopurine.

6. A process of claim 1, wherein the root formation is induced by treatment with auxins in a concentration of about 0.8 to 1.5 g/l.

7. A process of claim 6, wherein the auxin is indole butyric acid.

8. A process of claim 1, wherein the Pilocarpus cells are *Pilocarpus microphyllus* cells.

9. A process of claim 1, wherein the Pilocarpus cells are *Pilocarpus jaborandi* cells.

10. A process of claim 1, wherein the in vitro culture is obtained by inducing shoot differentiation of a callus, derived from an organ explant of Pilocarpus, on a series of nutrient media containing hormones.

11. A process of claim 10, wherein the shoot differentation is induced by a series of nutrient media containing, in the order indicated, the hormones
    a) α-naphthyl acetic acid, $N^6$-dimethylallyladenine and zeatine,
    b) 6-benzylaminopurine and/or
    c) 6-benzylaminopurine and indole-3-acetic acid.

12. A process of claim 10, wherein the shoot differentiation is induced by a series of nutrient media containing, in the order indicated, the hormones
    a) α-naphthyl acetic acid, $N^6$-dimethylallyladenine and zeatine and
    b) 6-benzylaminopurine.

* * * * *

UNITED STATES PATENT AND TRADEMARK OFFICE
CERTIFICATE OF CORRECTION

PATENT NO. : 5,059,531
DATED : October 22, 1991
INVENTOR(S) : REUTHER et al.

It is certified that error appears in the above-identified patent and that said Letters Patent is hereby corrected as shown below:

Col. 8; Line 3; Claim 2 reads ----

A process of claim the in vitro culture is a suspension culture.

should read - - - - -

A process of claim 1 wherein the in vitro culture is a suspension culture.

Signed and Sealed this

Second Day of February, 1993

Attest:

STEPHEN G. KUNIN

*Attesting Officer*       Acting Commissioner of Patents and Trademarks